(12) United States Patent
Zhao et al.

(10) Patent No.: US 8,097,417 B2
(45) Date of Patent: Jan. 17, 2012

(54) METHODS FOR DETECTING THERAPEUTIC EFFECTS OF ANTI-CANCER DRUGS BY MONITORING CHANGES IN GUT FLORA

(76) Inventors: Liping Zhao, Shanghai (CN); Wei Hua, Shanghai (CN); Xiaoyan Pang, Shanghai (CN); Jia Wei, Shanghai (CN); Dazheng Wu, Shanghai (CN)

( * ) Notice: Subject to any disclaimer, the term of this patent is extended or adjusted under 35 U.S.C. 154(b) by 0 days.

(21) Appl. No.: 12/380,103

(22) Filed: Feb. 23, 2009

(65) Prior Publication Data

US 2010/0112564 A1    May 6, 2010

(51) Int. Cl.
*C12Q 1/68* (2006.01)
*C12P 19/34* (2006.01)

(52) U.S. Cl. ..................... 435/6.12; 435/91.2
(58) Field of Classification Search ............... 435/6.12, 435/91.2
See application file for complete search history.

(56) References Cited

U.S. PATENT DOCUMENTS

| | | | | |
|---|---|---|---|---|
| 6,107,033 | A * | 8/2000 | Welling et al. ..................... | 435/6 |
| 2004/0170617 | A1 * | 9/2004 | Finegold ..................... | 424/93.45 |
| 2005/0026188 | A1 * | 2/2005 | Van Kessel et al. ............... | 435/6 |
| 2009/0170078 | A1 * | 7/2009 | Tsuji et al. ........................ | 435/6 |

OTHER PUBLICATIONS

Bingham, SA. (1999). "High-meat diets and cancer risk." Proceeding of the Nutrition Society 58(2): 243-8.
Lizuka, N., Hazama, S., Yoshimura, K., Yoshino, S., Tangoku, A., Miyamoto, K., Okita, K., and Oka, M. (2002). "Anticachectic effects of the natural herb Coptidis Rhizoma and Berberine on mice bearing colon 25/clone 20 adenocarcinoma." Int. J. Cancer 99, 286-291.
Jemal, A., Siegel, R., Ward, E., Hao, Y., Xu, J., Murray, T., and Thun, M. J. (2008). "Cancer statistics, 2008." CA Cancer J Clin 58(2): 71-96.
Katsuki, T., Hirata, K., Ishikawa, H., Matsuura, N., Sumi, S. , and Itoh, H. (2006). "Aged garlic extract has chemopreventative effects on 1,2-dimethylhydrazine-induced colon tumors in rats." J Nutr 136(3 Suppl): 847S-851S.
Kim, S.E., Shim, K.N., Jung, S.A., Yoo, K., and Moon I.H. (2007). "An association between obesity and the prevalence of colonic adenoma according to age and gender." J Gastroenterol 42(8): 616-23.
Larsson, S. C. and A. Wolk (2007). "Obesity and colon and rectal cancer risk: a meta-analysis of prospective studies." Am J Clin Nutr 86(3): 556-65.
Lee, K.J., Inoue, M., and Tsugane, S. (Jan. 6, 2007). "Physical activity and risk of colorectal cancer in Japanese men and women: the Japan public health center-based prospective study." Cancer Causes Control 18:199-209.
Moore, W. E. and Moore L.H. (1995). "Intestinal floras of populations that have a high risk of colon cancer." Appl Environ Microbiol 61(9): 3202-7.
Muyzer, G., De Waal, E. C., and Uitterlinder, A.G. (1993). "Profiling of complex microbial populations by denaturing gradient gel electrophoresis analysis of polymerase chain reaction-amplified genes coding for 16S rRNA." Appl Environ Microbiol 59(3): 695-700.
Nalini, N., Manju, V., and Menon, V.P. (2004). "Effect of coconut cake on the bacterial enzyme activity in 1,2-dimethyl hydrazine induced colon cancer." Clin Chim Acta 342(1-2): 203-10.
O'Keefe, S.J.D., Chung, D., Mahmoud, N., Sepulveda, A.R., Manade, M., Arch, J., Adada, H., and Van Der Merwe, T. (2007). "Why do African Americans get more colon cancer than Native Africans?" J Nutr 137(1 Suppl): 175S-182S.
Ogasawara, M., Matsubara, T , and Suzuki, H. (2001). "Inhibitory effects of evodiamine on in vitro invasion and experimental lung metastasis of murine colon cancer cells." Biol Pharm Bull 24(8): 917-20.
Ogasawara, M., Matsubara, T., Takahashi, S., Saiki, I., and Suzuki, H. (2002). "Anti-invasive and metastatic activities of evodiamine." Biol Pharm Bull 25(11): 1491-3.
Paskett, E.D., Reeves, K.W., Rohan, T.E., Allison, M.A., Willians, C.D., Messina, C.R., Whitlock, E., Sato, A., and Hunt, J.R. (2007). "Association between cigarette smoking and colorectal cancer in the women's health initiative." JNCI 99(22):1729-35.
Preslow, T.P., Barrow, B.J., Ashton, W.S., O'Riordan, M.A., Pretlow, T.G., Jurcisek, J.A., and Stellato, T.A.(1991). "Aberrant crypts: putative preneoplastic foci in human colonic mucosa." Cancer Res 51(5): 1564-7.
Shimizu, K., Das, S. K Baba, M., Matsuura, Y., and Kanazawa, K. (2006). "Dietary artepillin C suppresses the formation of aberrant crypt foci induced by azoxymethane in mouse colon." Cancer Lett 240(1): 135-42.
Terry, P., Ekbom, A., Lichtenstein, P., Feychting, M., and Wolk, A. (2001). "Long-term tobacco smoking and colorectal cancer in a prospective cohort study." Int J Cancer 91(4): 585-7.
Xiao, H., Hao, X., Simi, B., Ju, J., Jiang, H., Reddy, B.S., and Yang, C.S. (2008). "Green tea polyphenols inhibit colorectal aberrant crypt foci (ACF) formation and prevent oncogenic changes in dysplastic ACF in azoxymethane-treated F344 rats." Carcinogenesis 29(1): 113-9.

* cited by examiner

*Primary Examiner* — Kenneth Horlick (57) ABSTRACT

Non-invasive methods for monitoring the effect of an agent for treating colorectal cancer, comprising (1) collecting fecal samples from healthy subjects, subjects having precancerous lesions, and subject having precancerous lesions and being treated with an anti-cancer agent; (2) isolating total microbial genomic DNA from the fecal samples to provide total microbial genomic DNA; (3) comparing the total microbial genomic DNA using fingerprint spectrum analysis; (4) identifying key fingerprint bands correlated with the effect of the anti-cancer agent; (5) identifying key microorganisms associated with the key fingerprint bands; (6) designing microbial sequence-specific primers and probes; and (7) determining the quantitative differences of the key microorganisms in fecal samples to identify an indicator microorganism for monitoring the effect of the anti-cancer agent.

11 Claims, 6 Drawing Sheets

METHODS FOR DETECTING THERAPEUTIC EFFECTS OF ANTI-CANCER DRUGS BY MONITORING CHANGES IN GUT FLORA

CROSS-REFERENCE TO RELATED APPLICATION

The present application claims the benefit of foreign Application, CN 200810033742, filed Feb. 21, 2008, expressly incorporated herein by reference in its entirety.

FIELD OF THE INVENTION

The present invention relates to methods for monitoring the effects of drugs. Specifically, the present invention relates to non-invasive methods for monitoring effects of anti-cancer drugs using compositional changes of gut microorganisms.

BACKGROUND

Cancer is a major cause of death worldwide. Colorectal cancer is the third most common form of cancer that affects people's life and health. In China, the rising incidence of colorectal cancer relates to the improving quality of life in recent years. The risk factors for colorectal cancer development include dietary factors such as high fat, high protein, and low fibers diet, overweight, smoking, and the sedentary life style. Cancer chemoprevention and chemotherapy concern methods and agents that reduce the incidence or delay the onset of specific forms of cancer. The development of chemoprevention and chemotherapy strategies for cancer, such as colorectal cancer, requires effective methods for screening, identifying, and monitoring effect of cancer chemoprevention and chemotherapy methods and agents.

Epidemiological studies are currently used for evaluating, charactering, and monitoring the effects of cancer chemoprevention strategies. These methods often require large cohorts of population to whom one or more potential cancer chemoprevention methods or agents are given for 10 to 20 years of prolonged follow-ups. These methods often have perspective endpoints at which the incidence of cancer may be significantly reduced as compared to that in the subjects in control cohorts who do not receive cancer chemoprevention methods or agents. These longitudinal cohort studies are time-consuming and costly making them unrealistic for screening, identification, and monitoring candidate methods and agents for cancer chemoprevention and chemotherapy.

Some carcinogens can induce a large amount of aberrant crypt foci (ACF) in rats, such as azoxymethane (AOM) and 1,2-dimethylhydrazine (DMH). The presence of ACF may be the earliest pathological change in the development of colorectal cancer in rodents and humans (Shimizu et al. *Cancer Lett,* 1:135-142, 2006). The intervention of cancer chemoprevention agents in this rodent model reduces the number of ACF. This ACF-based rat model provides one method for identifying and characterizing agents for anti-cancer effects, including in colorectal cancer. However, these methods use invasive procedures involving euthanasia of model animals, such as rats and mice, and staining of gastrointestinal tract with methylene blue to determine the number of ACF before and after treatment with anti-cancer agents.

In 1995, Moor et al. recognized that the microbial compositions differed significantly in populations at high and low risk of colorectal cancer (Moor et al., Intestinal Floras of Populations That Have a High Risk of Colon Cancer, *Applied and Environmental Microbiology* 9:3202-3207, 1995). Approximately 500 species or $10^{14}$ the number of microorganisms live in the intestinal tract of host animals; and the microbial composition in fecal flora relates to the composition in gut flora. However, the composition of cultured fecal flora often differs from the composition in gut flora because, depending on the culture condition, certain microbial species may overgrowth whereas other certain microbial species may not grow, which often results in alterations of the microbial composition of the cultured fecal flora.

There exists a need for methods for detecting and monitoring the therapeutic effects of an anti-cancer agent that are noninvasive, efficient, and accurate. The present invention seeks to fulfill these needs and provides further related advantages.

SUMMARY OF THE INVENTION

The present invention provides methods for monitoring effects of anti-cancer agents using microbial composition of fecal flora. Specifically, the present invention provides methods for monitoring the effects of anti-cancer agents by monitoring the changes in the molecular ecology of gut flora.

In one aspect, the method comprises (1) collecting fecal samples from healthy subjects, subjects having precancerous lesions, and subjects having precancerous lesions and being treated with an anti-cancer agent; (2) isolating total microbial genomic DNA from the fecal samples; (3) comparing the total microbial genomic DNA using fingerprint spectrum analysis technique, using the V3 regions of 16S rDNA gene to differentiate the compositional differences in the fecal flora; (4) identifying key fingerprint bands correlated with the effect of the anti-cancer agent using partial least squares-discriminate analysis; (5) identifying key microorganisms associated with the key fingerprint bands; (6) designing microbial sequence-specific primers and probes based on the sequences of the key microorganisms; (7) determining the quantitative differences of the key microorganisms in the fecal samples using quantitative real-time PCR analysis to identify an indicator microorganism for monitoring the effects of the anti-cancer agent.

The indicator microorganism is the key microorganism that shows a quantitative difference between the fecal sample from the subjects having precancerous lesions and the fecal samples from both the healthy subjects and the subjects having precancerous lesions and being treated with an anti-cancer agent, but no quantitative difference between the fecal sample of the healthy subjects and the fecal sample of the subjects having precancerous lesions and being treated with an anti-cancer agent.

The subject may be a human or an animal. The number of the subjects in each group may be at least 2, preferably from 3 to 20.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawing, wherein.

DETAILED DESCRIPTION

The present invention provides non-invasive methods for monitoring effects of anti-cancer agents by monitoring the changes in the microbial composition of fecal flora.

In one aspect, the method comprises obtaining microbial total genomic DNA fingerprint of fecal samples, comparing the microbial total genomic DNA fingerprints, and identifying one or more key microorganisms that differ among fecal samples. The methods utilize various techniques including, but not limited to, the preparation and identification of microbial DNA, DNA amplification, quantitative real-time PCR, PCR-based denaturing/temperature gradient gel electrophoresis (PCR-DGGE/TGGE), partial least squares-discriminate analysis (PLS-DA), and multivariate statistical analysis.

In a preferred embodiment, the method comprises collecting fecal samples from three groups including healthy subjects, subjects at the risk of developing colorectal cancer, for example, as indicated by harboring precancerous lesions, and subjects at the risk of developing colorectal cancer and being treated with an anti-cancer agent; isolating total microbial genomic DNA from the fecal samples of all three groups; comparing the total microbial genomic DNA using fingerprint spectrum analysis technique to provide total microbial genomic DNA fingerprints; identifying key fingerprint bands correlated with the effect of the anti-cancer agent by analyzing the major band patterns of the DNA fingerprints; identifying key microorganisms associated with the key fingerprint bands; designing microbial sequence-specific primers and probes based on the sequences of the key microorganisms; and determining the quantitative differences of the key microorganisms among the fecal samples of all three groups by using quantitative real-time PCR analysis using the microbial sequence-specific primers and probes to identify an indicator microorganism for monitoring the effect of the anti-cancer agent. Preferably, the indicator microorganism is the key microorganism that shows a quantitative difference between the fecal sample of the subjects at risk of developing colorectal cancer and the fecal samples of both the healthy subjects and the subjects being treated with the anti-cancer agent and no quantitative difference between the fecal samples of the healthy subjects and the fecal samples of the subjects being treated with the anti-cancer agent.

In one embodiment, partial least squares-discriminate analysis may be used to analyze the major band patterns of the DNA fingerprints and identify the key fingerprint bands correlated with the effects of the anti-cancer agent. In one embodiment, the fingerprint spectrum analysis technique comprises amplifying the V3 regions of 16S rDNA gene to serve as a template to differentiate the microorganisms' compositional differences in the fecal flora.

The invention provides composition and methods of preparation, amplification, and characterization of fecal microbial total genomic DNA. In a preferred embodiment for collecting fecal samples and the extraction of total microbial genomic DNA, total microbial genomic DNA may be extracted from healthy individuals, individuals at the risk of colorectal cancer, for example, as indicated by harboring precancerous lesions, and individuals at the risk of colorectal cancer and being treated with one or more chemoprevention or chemotherapeutic agents, i.e., anti-cancer agents. In certain embodiments, DNA sequences in the V3 region of 16S rDNA gene in microbial species are amplified and the resultant PCR products are separated in PCR-based DGGE gel analysis. The DGGE image profile provides DNA fingerprints in the V3 region of 16S rDNA of the fecal flora. In another preferred embodiment, partial least squares-discriminate analysis (PLS-DA) of the relative distances or positions and intensity of bands in the DGGE image profile may be used to identify the differences in the quantity and/or species of microorganisms in the fecal and, therefore, gut, flora.

DNA fingerprint of microbial species in an individual's fecal sample correlates with the microbial composition in the gut flora of the individual. In a preferred embodiment, main components of DNA fingerprint are characteristic among the subjects of the same cohort but different among the subjects of different cohorts, for example, the healthy cohorts versus the cohorts having precancerous lesions. It is noted that the main components of DNA fingerprint that is characteristic to the subjects having precancerous lesions reverse their compositional changes in the subjects having precancerous lesion but being treated with anti-cancer agents.

In another embodiment, the invention provides compositions and methods for validation and quantification of the main characteristic bands in PCR-DGGE profiling of DNA fingerprint in the V3 region of 16S rDNA gene. In a preferred embodiment, main components of DNA fingerprint are excised, purified, and cloned into a vector library for purification and sequencing of inserts or sequences representing the main components of DNA fingerprint. These sequences relate to certain microbial species in gut flora with which microbial species-specific primers and probes may be designed for classification and quantification of the microbial species represented by the main components of DNA fingerprint. Fluorescence and quantitative real-time PCR analyses provide validation and quantification of certain microbial species in fecal flora. The quantitative differences of microbial species shown among the subjects of different cohorts (groups), such as the healthy individuals, the individuals at the risk of colorectal cancer, for example, as demonstrated by having precancerous lesions, and the individuals at the risk of colorectal cancer and being treated with anti-cancer agents.

The quantitative change of the microbial species is indicative of the effects of anti-cancer agents.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effects of Traditional Chinese Medicine on Colorectal Cancer Chemoprevention in Rats 27 male Wistar rats (80~100 grams) were purchased from SLAC Shanghai Laboratory Animals, Ltd. and housed in a special-pathogen-free (SPF) facility at Shanghai University of Traditional Chinese Medicine, where the temperature variation was between 20° C. and 25° C., the relative humidity was between 40% and 70%, the day/night cycle was 12 hours, and the cages were made of bottomless and stainless steel. Animal care and experimental procedures complied with "The Standards for Animal Environment and Procedure in the People's Republic of China".

The rats were randomly divided into 4 groups: 6 for the healthy control group, 7 for the group harbored colorectal precancerous lesions, 7 for the group being treated with *Coptis Chinensis* (Huang Lian) and *Evodia Rutaecarpa* (Wu Zhu Yu) water extract (CEWE), a Traditional Chinese Medicine (TMC) herbal compound medicine, and 7 for the group being treated with a compound medicine, JIN FU KANG™ (JFK), a formulated TCM. On the first day of the second week after the rats adjusted to the new environment, DMH (30 mg/kg body weight) was injected (dorsal back s.q.) in the rats in 3 experimental groups, whereas the buffer (25 mM EDTA, 127 mM NaCl) was injected (dorsal back s.q.) into the rats in the control group. The injection was repeated once within the following week. *Coptis Chinensis* (Huang Lian) and *Evodia Rutaecarpa* (Wu Zhu Yu) water extract were administered daily by oral gavage (0.3 g/kg body weight) to the rats of the corresponding group beginning with the first DMH injection until the end of the experiment. The compound medicine, JIN FU KANG™, was administered daily by oral gavage (1.33 g/kg body weight) to the rats of the corresponding group beginning with the first DMH injection until the end of the experiment. On the $10^{th}$ week, all rats were euthanized, the intestinal tract was dissected, fixed in 10% formalin overnight, stained with 0.2% methylene blue for 10~20 minutes, and the number of ACF per tract was counted using an inverted microscope (40×).

The average number of ACF per tract were insignificant in the control group, 37.7±2.6 in the ACF model group, 16.7±1.2 in the *Coptis Chinensis* (Huang Lian) and *Evodia Rutaecarpa* (Wu Zhu Yu) water extracts (CEWE) treated group, and 15.1±2.9 in the compound medicine, Jin Fu Kang™, treated group. The Mann-Whitney analysis using SPSS 12.0 statistics software revealed that both treated group showed a statistically significant reduction in the number of ACF per tract ($P<0.05$).

Example 2

Identification of DNA Fingerprints in Fecal Microbial Total Genomic DNA

Fresh fecal samples were collected from all 4 groups of rats on the $9^{th}$ week and stored in −20° C. freezer. Fecal microbial total genomic DNA was isolated using a commercially available kit (QIAGEN). PCR-based DNA amplification of this region enriches a highly variable region of the 16S rDNA gene that provides a good indication of phylogenetic affiliation of bacterial species (Muyzer et al., Profiling of Complex Microbial Populations by Denaturing Gradient Gel Electrophoresis Analysis of Polymerase Chain Reaction-Amplified Genes Coding for 16S rRNA, *Applied and Environmental Microbiology*, 59(3), 695-700, 1993). The sequences for PCR primers were adopt from Muyzer et al. The 25 µl PCR amplification reaction system comprises of: 0.5 µl of 25 µmol/L primer P2, 5'-ATTACCGCGGCTGCTGG-3, and P3: 5'-CGCCCGCCGCGCGCG-GCGGGCGGGGCGGGGGCACGGGGGGC-CTACGGGAGGCAGCAG-3', 2 µl of 2.5 µmol/L dNTPs, 20 ng of template DNA, 0.625 u of rTaq DNA polymerase, and 1× buffer for the remaining volume. The cycling program for PCR amplification includes these steps: 4 minutes of initial denaturation at 94° C., followed by 25 cycles of 1 minute of denaturing step at 94° C., 1 minute of annealing (for the first 20 cycles, the annealing temperature drops 1° C. for every 2 cycles from 65° C. down to 56° C., and for the remaining 5 cycles, the annealing temperature is maintained at 55° C.), and 1 minute of extension at 72° C., and finally, 10 minutes of elongation at 72° C.

PCR-DGGE analysis using Decode DGGE (denaturing gradient gel electrophoresis) apparatus (Bio-Rad, Inc., Hercules, Calif.) established DNA fingerprints of the V3 region of 16S rDNA in fecal flora. The DGGE solution system comprised of a denaturing gradient in the range of 26.5% to 52% that was prepared by diluting 8% polyacrylamide gel with denaturants, 7M urea and 40% de-ionized formamide, with the gel without denaturants, and electrophoresis running buffer, 1×Tris-acidic acid-EDTA (TAE) (pH8.4). The DGGE analysis was performed at 200 v, 60° C., for 240 minutes. After the electrophoresis, the DGGE gel was stained with SYBR GREEN I (N',N'-dimethyl-N-[4-(E)-(3-methyl-1,3,-benzothiazol-2-ylidene)methyl)-1-phenylquinolin-1-ium-2-yl]-N-propylpropane-1,3-diamine) fluorescent dye (Amresco, Solo, Ohio) followed by gel visualization using UVI gel documentation system (UVI tec, Cambridge, UK).

DGGE results were digitalized and QUANTITY ONE® v4.4 software (Bio-Rad, Hercules, Calif.) was used to reduce noise signals, record the migration of each band, and calculate the percentage of brightness for each band. DNA fingerprint for each animal was transformed into a cluster of multidimensional variants of which each dimension represented either a migration or a value of brightness.

Figure 1:
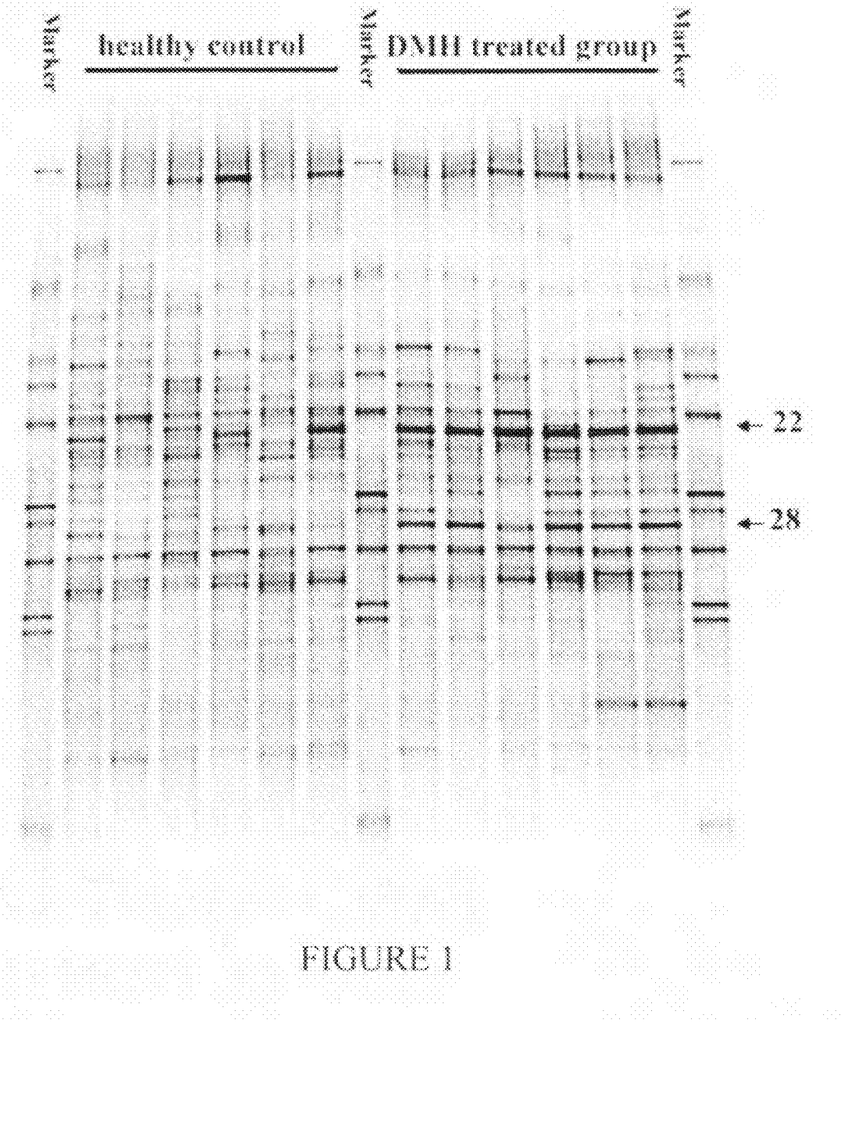
FIG. 1 shows the results of the PCR-DGGE analysis of DNA fingerprints in the V3 region of 16S rRNA gene in fecal floras from 6 DMH-treated rats having precancerous lesions and 6 healthy control rats on the 9$^{th}$ week.
Figure 2:
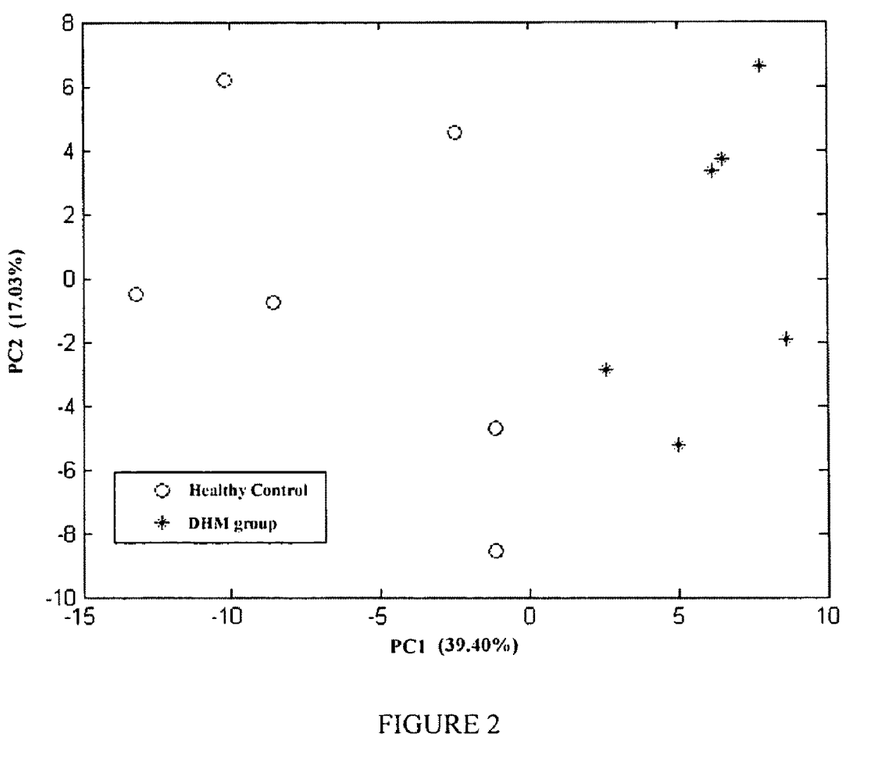
FIG. 2 shows the results of the scaling analysis of PCR-DGGE profiles including the main components of DNA fingerprints in the V3 region of 16S rDNA in fecal floras from 6 DMH-treated rats having precancerous lesions and 6 healthy control rats on the 9$^{th}$ week.

The PCR-DGGE image shown in FIG. 1 revealed DNA fingerprint of the V3 region of 16S rDNA gene for each of 6 healthy rats in control group and 6 rats in DMH-treated group (FIG. 1). While the healthy rats showed diverse bacterial compositions, DMH-treated rats displayed a cluster of predominant bands with similar migration and increased brightness indicting the presence of overgrown bacterial species. In addition to the parameters of band migration and brightness, the presence of precancerous lesions was introduced for PLS-DA analysis by giving an eigenvalue of 0 and +1 for the healthy rats and DMH-treated rats, respectively. With the integration of Y variables and DNA fingerprint parameters, PLS-DA can differentiate bacterial compositional changes in fecal flora from the healthy rats and the rats harboring precancerous lesions. Multivariate statistical analysis indicated the significant difference in the composition of predominant bacterial species in these two groups of rats (FIG. 2).

Figure 3:
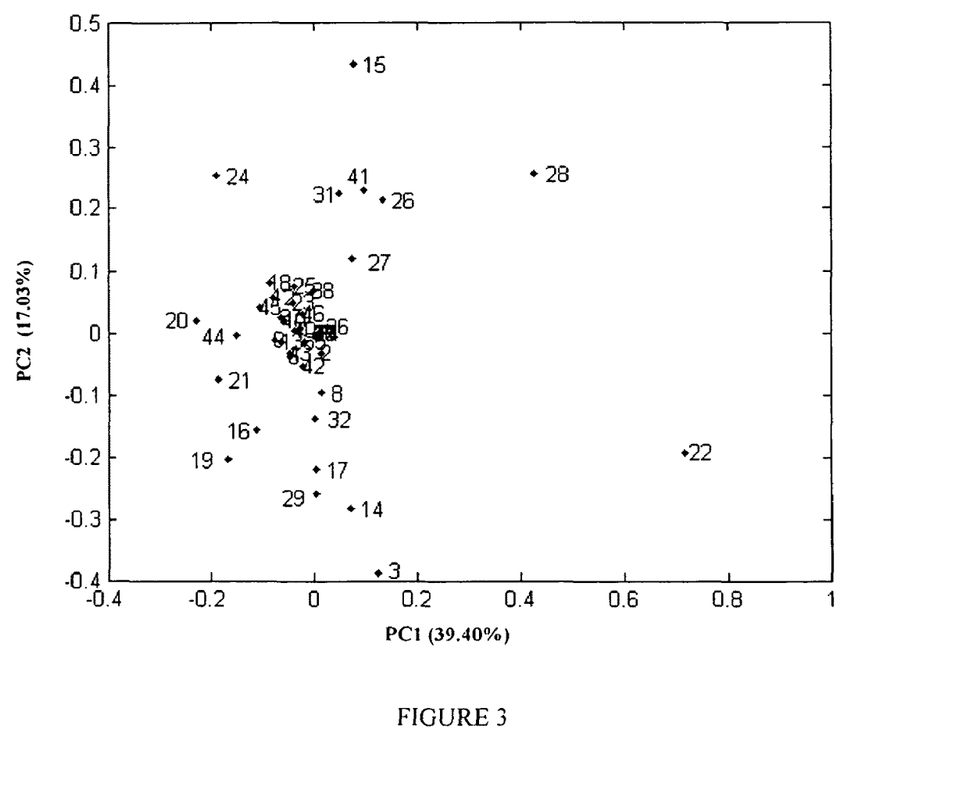
FIG. 3 shows the results of the loading analysis of PCR-DGGE profiles having the main components of DNA fingerprints in the V3 region of 16S rDNA in fecal floras from 6 DMH-treated rats having precancerous lesions and 6 healthy control rats on the 9$^{th}$ week.
Figure 4:
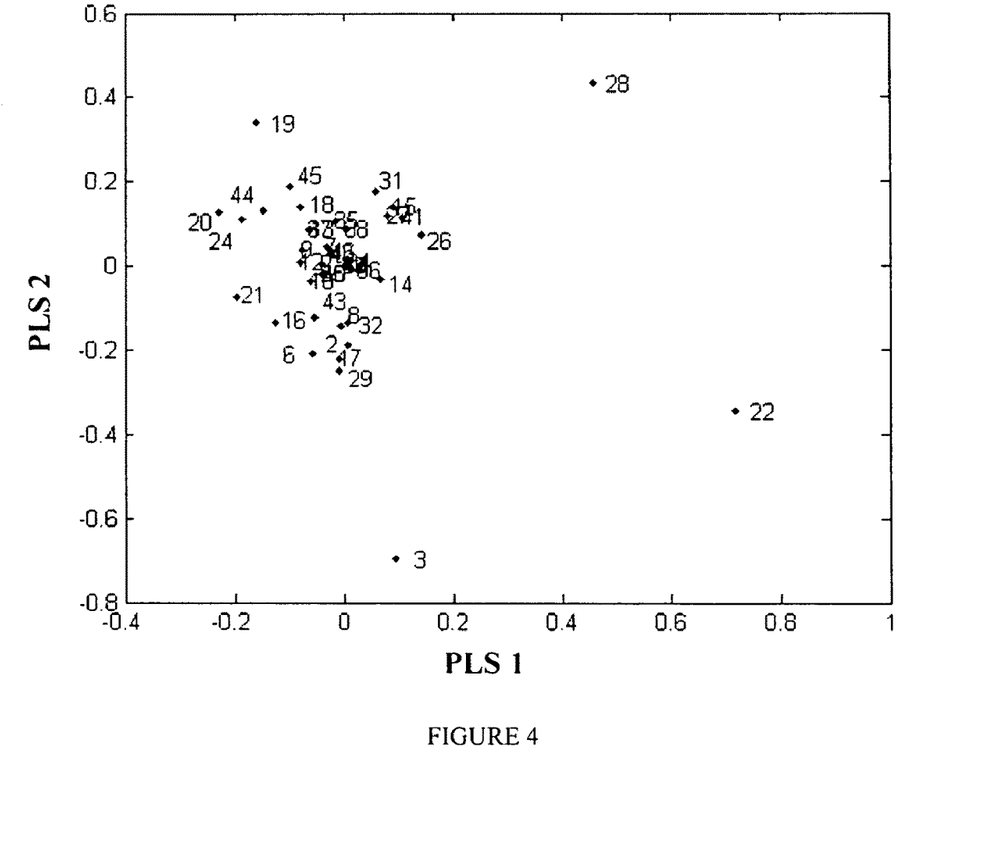
FIG. 4 shows the results of the PLS-DA analysis of PCR-DGGE profiles comprising the main components of DNA fingerprints in the V3 region of 16S rDNA in fecal floras from 6 DMH-treated rats having precancerous lesions and 6 healthy control rats on the 9$^{th}$ week.

The DGGE band brightness or band load represented compositional changes in the bacterial species between the healthy rats and rats harboring precancerous lesions leading to the presence of predominant bacterial species revealed by using both principal component analysis and PLS analysis. The band load of the two bands, v3-22 and v3-28, was greater than 0.4 (FIGS. 3 and 4) demonstrating that at least two groups of bacterial species represented by these two bands mark the compositional change between the healthy group and DMH-treated group.

Figure 5:
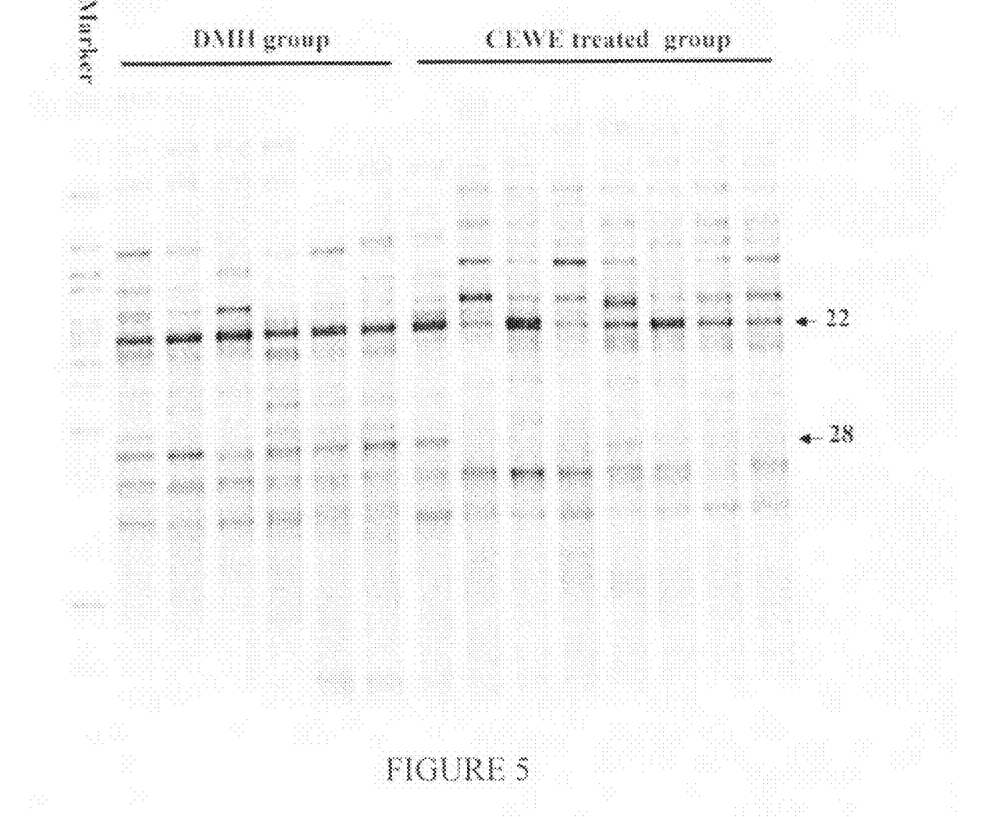
FIG. 5 shows the results of the PCR-DGGE analysis of DNA fingerprints in the V3 region of 16S rDNA in fecal floras on the 9$^{th}$ week from 6 DMH-treated rats having precancerous lesions and 6 DMH-treated rats having precancerous lesions and being treated with an anti-cancer mixture, *Coptis Chinensis* (Huang Lian) and *Evodia Rutaecarpa* (Wu Zhu Yu) water extracts (CEWE), for 9 weeks.
Figure 6:
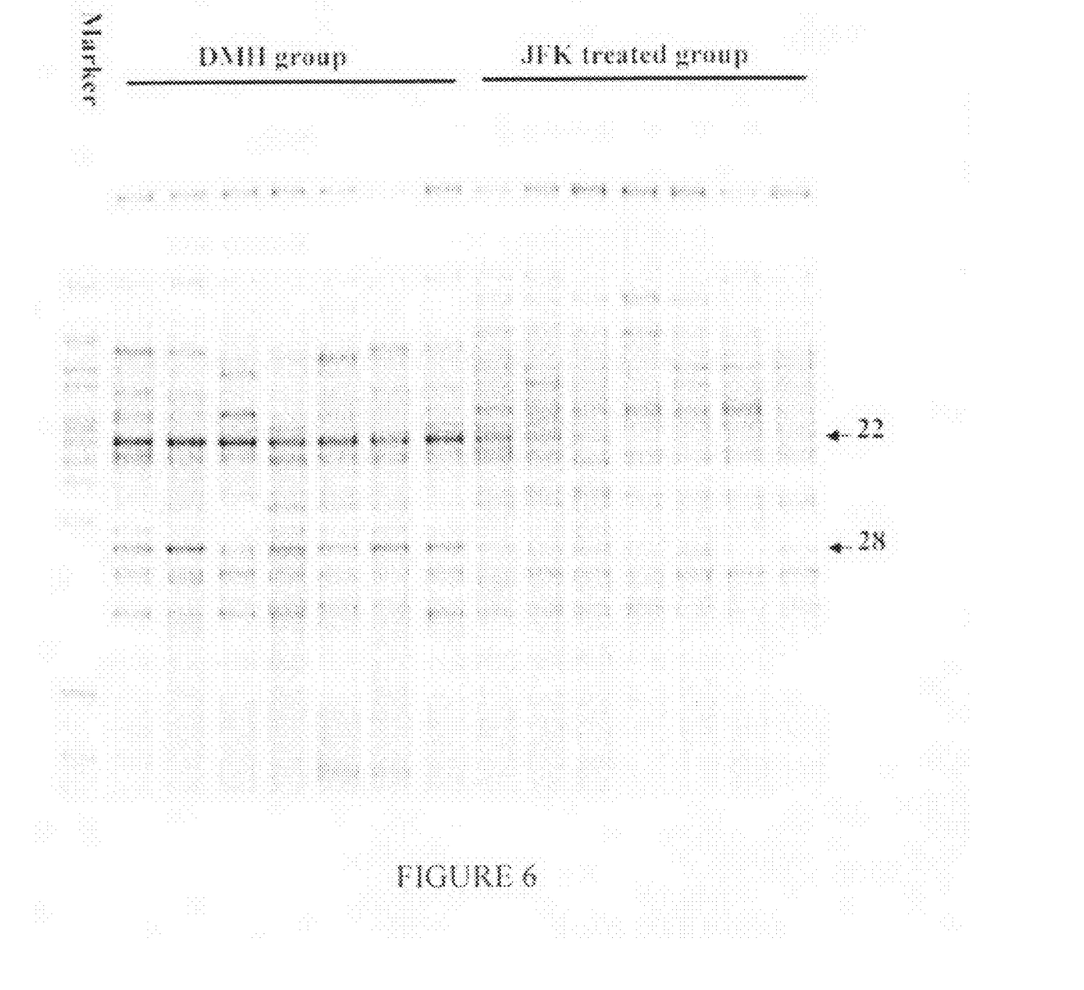
FIG. 6 shows the results of the PCR-DGGE analysis of DNA fingerprints in the V3 region of 16S rDNA in fecal floras on the 9$^{th}$ week from 6 DMH-treated rats having precancerous lesions and 6 DMH-treated rats being treated with an anti-cancer compound medicine, Jin Fu Kang (JFK, Golden rehabilitation), for 9 weeks.

The intervention of cancer chemoprevention reduced the number of ACF as shown in Example 1. Accordingly, the band load of the two bands, v3-22 and v3-28, was clearly reduced in the rats in both *Coptis Chinensis* (Huang Lian) and *Evodia Rutaecarpa* (Wu Zhu Yu) water extracts (CEWE)-treated and the compound medicine JIN FU KANG™-treated groups when compared to DMH-treated rats (FIGS. 5 and 6). In a previous example, the band load of these two bands related to the risk of ACF and cancer. These two examples were preferred embodiments of identification and use of compositions and methods of this invention for monitoring and validation of colorectal cancer chemoprevention agents. The predominant bands that were consistently present in the rats harboring precancerous lesions were attenuated in the rats being treated with cancer chemoprevention agents, either *Coptis Chinensis* (Huang Lian) and *Evodia Rutaecarpa* (Wu Zhu Yu) water extracts or the compound medicine JIN FU KANG™. The reversal of the two DGGE bands provides a preferred indicator for monitoring effects of cancer chemoprevention agents by using PCR-DGGE analysis.

Example 3

Identification of Bacterial Species Represented by the Two DGGE Bands

Band excision. The two predominant bands, v3-22 and v3-28, in the DGGE gel were excised by using a sterile blade, sliced in fine pieces, suspended in 100 µl of distilled $H_2O_2$ in a 1.5 ml Eppendorf tube, and store at 4° C. for 16 hours.

Cloning. The cloning strategy starts with PCR amplification of an excised band by using the same PCR reaction system and cycling steps for DGGE analysis. PCR products were purified by using 2% agarose gel electrophoresis, the band with an expected size was excised, DNA fragments were extracted by using a gel recovering kit (Axygen, USA), purified DNA was suspended in 100 µl of distilled $H_2O_2$, and its DNA concentration was determined. The agarose gel-purified DNA fragments were ligated into a cloning vector. The ligation reaction consisted of 5 µl of 2× ligation buffer, 1 µl of pGEM-T easy vector (50 ng/µl)(Promega), 10~20 ng of DNA fragments/inserts, and 1 µl of T4 DNA ligase (2 Weiss u/µl) in a total 10 µl volume in distilled $H_2O_2$, and was well-mixed and incubated at 4° C. for 16 hours. The ligation mixture was used for transformation into DH5a competent cells of *Escherichia coli* (Shanghai Tian Gan Biotechnology, $10^6$ transformation frequency) through heat shock and the cell mixture was spread onto a LB plate containing 80 µg/ml X-gal (5-bromo-4-chloro-3-indolyl-β-D-galactopyranoside), 1 mM IPTG(isopropyl-β-D-thiogalactopyranoside), and 100 µg/ml ampicillin.

Sequencing. White colonies were harvested and saved in LB solution containing 100 µg/ml ampicillin and 15% glycerol and stored in −70° C. The plasmid DNA was extracted by using the boiling method following 10 minutes boiling, 5 minutes cooling on ice, and 10 minutes spin at 3000 rpm. The purified plasmid DNA was suspended in 30 µl distilled $H_2O_2$ and 1 µl of clear supernatant was used as the template for PCR amplification and DGGE analysis, as previously described. When the size of PCR product matched to one of the predominant DGGE bands, the insert of the plasmid DNA was sequenced. The plasmid carrying an insert with an expected size were sequenced (Shanghai Ying Jun Biotechnology).

BioEdit software was used to remove the vector's sequences and the software provided by RDP was used to remove chimera artifacts in the sequences. The sequences of the insert of interest were aligned with all available sequences of bacterial species in the databanks in both GenBank (www.ncbi.nlm.nih.gov/BLAST/) and RDP (http://rdp.cme.msu.edu) in order to identify the bacterial species or its closest related species. Table 1 summarizes the result of sequencing analysis.

TABLE 1

Identification of the bacterial species represented by the two predominant bands in the DGGE-based DNA fingerprint profile.

| DGGE Band | GenBank Accession | Closest Relative | Similarity |
|---|---|---|---|
| V3-22 | EF062467 | *Ruminococcus obeum* (X85101) | 98% |
| V3-28 | EF062468 | *Allobaculum stercoricanis* (AJ417075) | 95% |

Accession numbers for cancer chemoprevention-related DGGE bands. The sequences of the bacterial species represented by the two predominant bands and related to the intervention of the two anti-cancer agents, *Coptis Chinensis* (Huang Lian) and *Evodia Rutaecarpa* (Wu Zhu Yu) water extracts, and the compound medicine JIN FU KANG™, were deposited in GenBank and their accession numbers are EF062467 and EF062468.

Example 4

Quantification of the Bacterial Species Sensitive to Cancer and Cancer Chemoprevention The predominant band, v3-22, shared a 98% sequence homology with *Ruminococcus obeum* with which two bacterial sequence-specific primers were designed, ROB3: 5'-TGAGGAGACTGCCAGGGA-3' and ROB2: 5'-CTCCT-TCTTTGCAGTTAGGT-3', and used for a quantitative PCR analysis. A standard curve for PCR template was established by using 10× diluted plasmid DNA of which the copy numbers ranged from $1.23 \times 10^9$ to $1.23 \times 10^3$. The 25 µl fluorescent-based quantitative PCR reaction consisted of: 12.5 pmol each primer, 200 µmol/L each dNTP, 20 ng each template DNA, 1.5 u rTaq DNA polymerase in 1× polymerase buffer, and 1×SYBR Green I fluorescent dye. The amplification was performed in a real-time fluorescence quantitative PCR system (MJ Research) following: 3 minutes of denaturing at 94° C., 40 cycles of denaturing step at 94° C. for 30 seconds, annealing step at 59° C. for 30 seconds, extension step at 72° C. for 30 seconds, and reading step at 82° C. for 10 seconds during which fluorescent signals were collected, and 5 minutes of final extension at 72° C. Each sample was repeated for 3 times and the difference in the number of *R. obeum* in the digestive tract of healthy animals, animals harbored precancerous lesions, and animals treated with anti-cancer agents was determined.

As to the predominant band, v3-28, the bacterial sequence-specific primers and probe were designed based on its homologous sequences in the databanks in GenBank (http://www.ncbi.nlm.nih.gov/BLAST/) and RDP (http://rdp.cme.msu.edu) and by using Primer Expression 2.0 software, v328-FP: 5'-GGCGAGGTACCATCAAAACG-3', v328-RP: 5'-FAM-TCATTTCCTCTTCCGTTCCTTTTT-TAMRA-3', TaqMan probe: 5'-FAM-TCATTTCCTCTTCCGTTC-CTTTTT-TAMRA-3'. FAM is a 5' fluorescence reporter tag, 6-Carboxy-fluorescein; and TAMRA is a 3' quenching fluorescence tag, 6-Carboxy-tetramethylrhodamine. A standard curve for PCR template was established by 10× dilution of the plasmid DNA with its copy numbers from $1.23 \times 10^9$ to $1.23 \times 10^3$. The 25 µl fluorescent-based quantitative PCR reaction was composed of: 12.5 pmol each primer and probe, 200 µmol/L each dNTP, 20 ng each template DNA, and 1.75 u rTaq DNA polyermase in 1× polymerase buffer. The amplification was performed in a real-time fluorescence quantitative PCR system (MJ Research): 3 minutes of denaturing at 94° C., 40 cycles of denaturing step at 94° C. for 30 seconds, annealing step at 59° C. for 30 seconds, extension step at 72° C. for 30 seconds, fluorescent signals were collected at the end of each cycle, and 5 minutes of final extension at 72° C. Each sample was repeated for 3 times. The numbers of this bacterial specie in all 4 groups of rats in the $9^{th}$ week were determined.

SPSS 12.0 software was used to perform the statistical analysis of the quantitative real-time PCR results. The result of this analysis indicated that the number of *R. obeum* in DMH-treated group, which harbored precancerous lesions, was significantly higher than that in the healthy rats ($p<0.05$, one-way ANOVA). The numbers of *R. obeum* in *Coptis Chinensis* (Huang Lian) and *Evodia Rutaecarpa* (Wu Zhu Yu) water extracts-treated group and the compound medicine JIN FU KANG™-treated group were significantly lower than that in DMH-treated group ($p<0.05$), but were similar to that in the control group ($p>0.05$).

Similar to the band, v3-22, the number of v3-28-related bacteria specie in DMH-treated group (i.e., harbored precancerous lesions) was significantly higher that that in the healthy rats ($p<0.05$, one-way ANOVA). The numbers of *R. obeum* in *Coptis Chinensis* (Huang Lian) and *Evodia Rutaecarpa* (Wu Zhu Yu) water extracts-treated group and the compound medicine JIN FU KANG™-treated group were significantly lower than that in DMH-treated group ($p<0.05$), but were similar to that in the control group ($p>0.05$).

These results indicate that the numbers of bacteria species in gut flora represented by the two predominant bands, v3-22 and v3-28, were significantly increased in the rats harbored precancerous lesions due to DMH treatment. Apparently, the intervention of anti-cancer agents, such as *Coptis Chinensis* (Huang Lian) and *Evodia Rutaecarpa* (Wu Zhu Yu) water extracts, and the compound medicine JIN FU KANG™, alleviate the lesions in colon and result in a reduction in the numbers of the two bacteria species. Thus, monitoring the change in band load could be non-invasive, feasible, and efficient molecular method for monitoring effects of cancer chemoprevention agents.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A non-invasive method for monitoring the effects of an agent for treating colorectal cancer, comprising:
   (1) collecting fecal samples from a first group of subjects, a second group of subjects, and a third group of subjects to provide a first group of fecal samples, a second group of fecal samples, and a third group of fecal samples, respectively,
   wherein the first group of subjects consists of a plurality of healthy subjects, the second group of subjects consists of a plurality of subjects at risk of developing colorectal cancer, and the third group of subjects consists of a plurality of subjects at risk of developing colorectal cancer and being treated with an anti-cancer agent;
   (2) isolating total microbial genomic DNA from the first group of fecal samples, the second group of fecal samples, and the third group of fecal samples to provide a first group of total microbial genomic DNA, a second group of total microbial genomic DNA, and a third group of total microbial genomic DNA, respectively;
   (3) comparing the first group of total microbial genomic DNA, the second group of total microbial genomic DNA, and the third group of total microbial genomic DNA using fingerprint spectrum analysis technique to provide a first group of fingerprints, a second group of fingerprints, and a third group of fingerprints,
   wherein the fingerprint spectrum analysis technique comprises amplifying the V3 regions of 16S rDNA gene to serve as a template to differentiate the compositional differences in the fecal flora of the first group of fecal samples, the second group of fecal samples, and the third group of fecal samples;
   (4) identifying key fingerprint bands correlated with the effect of the anti-cancer agent by analyzing the major band patterns of the first group of fingerprints, the second group of fingerprints, and the third group of fingerprints using partial least squares-discriminate analysis;
   (5) identifying key microorganisms associated with the key fingerprint bands;
   (6) designing microbial sequence-specific primers and probes based on the sequences of the key microorganisms;
   (7) determining the quantitative differences of the key microorganisms in the first group of fecal samples, the second group of fecal samples, and the third group of fecal samples using quantitative real-time PCR analysis using the microbial sequence-specific primers and probes to identify an indicator microorganism for monitoring the effect of the anti-cancer agent,
   wherein the indicator microorganism is the key microorganism that shows a quantitative difference between the second group of fecal samples and both the first group and the third group of fecal samples and no quantitative difference between the first group of fecal samples and the third group of fecal samples.

2. The method of claim 1, wherein the fingerprint spectrum analysis technique comprises amplifying the genomic sequences of the V3 regions of 16S rDNA gene using PCR-TGGE/DGGE fingerprinting technique.

3. The method of claim 2, wherein the PCR-TGGE/DGGE fingerprinting technique comprises amplifying the V3 regions of 16S rDNA gene using a primer P2 having a sequence 5'-ATTACCGCGGCTGCTGG-3' (SEQ ID NO 8) and a primer P3 having a sequence 5'-CGCCCGC-CGCGCGCG- GCGGGCGGGGCGGGGGCACGGGGGGC-
CTACGGGAGGCAGCAG-3' (SEQ ID NO 9), and using the PCR product from the V3 regions of 16S rDNA gene for PCR-DGGE fingerprint analysis.

4. The method of claim 1, wherein amplifying the V3 regions of 16S rDNA gene comprises a procedure including (i) 4 minutes of initial denaturation of gene at 94° C., (ii) followed by 25 cycles wherein each cycle comprises 1 minute of denaturation of gene at 94° C., 1 minute of annealing, and 1 minute of extension at 72° C., wherein, for the first 20 cycles, the annealing temperature drops 1° C. for every 2 cycles from 65° C. down to 56° C., and for the remaining 5 cycles, the annealing temperature is maintained at 55° C., and (iii) 10 minutes of elongation at 72° C.

5. The method of claim 1, wherein each DNA fingerprint is converted to a multidimensional scaling plot, wherein each fingerprint band migration position represents a dimension, and the ratio of each fingerprint band intensity to the total fingerprint bands intensity represents a dimensional value.

6. The method of claim 2, wherein identifying key fingerprint bands correlated with the effect of the anti-cancer agent is carried out by using a computer.

7. The method of claim 2, wherein identifying key fingerprint bands correlated with the effect of the anti-cancer agent comprises identifying the microorganisms' compositional difference between the first group of fecal samples and the second group of fecal samples.

8. The method of claim 2, wherein determining the quantitative differences of the key microorganisms in the first group of fecal samples and the second group of fecal samples comprises analyzing the fingerprint bands using partial least squares-discriminate analysis to identify predominant bands representing the key microorganisms differentiating the first group of fecal samples and the second group of fecal samples.

9. The method of claim 2, wherein the indicator microorganism is the microorganism represented by a fingerprint band that differs between the first group of fingerprints and the second group of fingerprints, and shows no quantitative difference between the third group of fingerprints and the first group of fingerprints.

10. The method of claim 2, wherein identifying key microorganisms associated with the key fingerprint bands comprises excising the key fingerprint bands from the fingerprints to provide excised bands, recovering microbial DNA fragments from the excised bands, establishing a microbial DNA fragments library, comparing the size of the microbial DNA fragments with the original fingerprints, and sequencing the microbial DNA fragments.

11. The method of claim 1, wherein the microbial sequence-specific primers and probes comprise (i) *R. obeum*-specific primers having the sequences ROB3: 5'-TGAG-GAGACTGCCAGGGA-3' (SEQ ID NO 6), ROB2: 5' CTC-CTTCTTTGCAGTTAGGT-3' (SEQ ID NO 7), and (ii) primers for V3-28 band having the sequences: v328-FP, 5'-GGCGAGGTACCATCAAAACG-3'(SEQ ID NO 3); v328-RP, 5'TCGGGTCGTAAAGCTCTGTTG-3' (SEQ ID NO 4); and (iii) the TaqMan probe sequence: 5' FAM-TCATTTCCTCTTCCGTTCCTTTTT-TAMRA 3' (SEQ ID NO 5).

* * * * *

SEQUENCE LISTING

<160> NUMBER OF SEQ ID NOS: 5

<210> SEQ ID NO 1
<211> LENGTH: 170
<212> TYPE: DNA
<213> ORGANISM: Ruminococcus obeum

<400> SEQUENCE: 1

```
cctacgggag gcagcagtgg ggaatattgc acaatggggg aaaccctgat gcagcgacgc      60
cgcgtgaagg aagaagtatc tcggtatgta aacttctatc agcagggaag atagtgacgg     120
tacctgacta agaagccccg gctaactaaa gtgccagcag ccgcggtaat                170
```

<210> SEQ ID NO 2
<211> LENGTH: 194
<212> TYPE: DNA
<213> ORGANISM: Allobaculum stercoricanis
<220> FEATURE:
<223> OTHER INFORMATION: May be used for identifying and monitoring
      gut microbiota population

<400> SEQUENCE: 2

```
cctacgggag gcagcagtag ggaattttcg tcaatgggcg caagcctgaa cgagcaatgc      60
cgcgtgagtg aggaaggcct tcgggtcgta aagctctgtt gcgagggaaa aaggaacgga     120
agaggaaatg attccgtttt gatggtacct cgccagaaag tcacggctaa ctacgtgcca     180
gcagccgcgg taat                                                       194
```

```
<210> SEQ ID NO 3
<211> LENGTH: 20
<212> TYPE: DNA
<213> ORGANISM: Allobaculum stercoricanis
<220> FEATURE:
<223> OTHER INFORMATION: may be used for identifying and monitoring
      gut microbiota population

<400> SEQUENCE: 3
ggcgaggtac catcaaaacg                                            20

<210> SEQ ID NO 4
<211> LENGTH: 21
<212> TYPE: DNA
<213> ORGANISM: Allobaculum stercoricanis
<220> FEATURE:
<223> OTHER INFORMATION: may be used for identifying and monitoring
      gut microbiota population

<400> SEQUENCE: 4
tcgggtcgta aagctctgtt g                                          21

<210> SEQ ID NO 5
<211> LENGTH: 24
<212> TYPE: DNA
<213> ORGANISM: Allobaculum stercoricanis
<220> FEATURE:
<223> OTHER INFORMATION: Maybe used for identifying and monitoring gut
      microbiota population

<400> SEQUENCE: 5
tcatttcctc ttccgttcct tttt                                       24
```